United States Patent
Mori et al.

(10) Patent No.: US 6,829,324 B2
(45) Date of Patent: Dec. 7, 2004

(54) X-RAY CT SCANNER CAPABLE OF PERFORMING IMPROVED LOG CONVERSION

(75) Inventors: Issei Mori, Tochigi-ken (JP); Akira Adachi, Otawara (JP); Masahiro Kazama, Tochigi-ken (JP); Satoshi Saito, Kuroiso (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 12 days.

(21) Appl. No.: 10/269,070

(22) Filed: Oct. 11, 2002

(65) Prior Publication Data

US 2003/0156679 A1 Aug. 21, 2003

(30) Foreign Application Priority Data

Feb. 19, 2002 (JP) ...................................... P2002-041166
Sep. 30, 2002 (JP) ...................................... P2002-287330

(51) Int. Cl.[7] ................................................. A61B 6/00
(52) U.S. Cl. .............................. 378/4; 378/901; 378/19
(58) Field of Search ............................... 378/4, 901, 19

(56) References Cited

U.S. PATENT DOCUMENTS

| | | | |
|---|---|---|---|
| 4,369,509 A | | 1/1983 | Akagiri |
| 5,615,279 A | | 3/1997 | Yoshioka et al. |
| 6,201,849 B1 | * | 3/2001 | Lai ............................... 378/4 |
| 6,278,762 B1 | * | 8/2001 | Hu ............................... 378/15 |
| 6,385,278 B1 | * | 5/2002 | Hsieh ............................ 378/8 |
| 6,415,013 B1 | * | 7/2002 | Hsieh et al. .................. 378/19 |
| 6,490,335 B1 | * | 12/2002 | Wang et al. .................. 378/15 |
| 6,519,314 B1 | | 2/2003 | Baba et al. |

FOREIGN PATENT DOCUMENTS

| | | |
|---|---|---|
| EP | 0 098 633 | 1/1984 |
| EP | 62115965 | 5/1987 |
| EP | 2001119583 | 4/2001 |
| JP | 5-261093 | 10/1993 |
| JP | 7-222741 | 8/1995 |
| JP | 9-168536 | 6/1997 |
| JP | 2002-119504 | 4/2002 |

* cited by examiner

Primary Examiner—David V. Bruce
Assistant Examiner—Irakli Kiknadze
(74) Attorney, Agent, or Firm—Oblon, Spivak, McClelland, Maier & Neustadt, P.C.

(57) ABSTRACT

An X-ray CT scanner comprises an X-ray source generating an X-ray, detector detecting the X-ray transmitted through an object, processor to produce projection data, and reconstruction unit to reconstruct an image using the projection data. The processor produces the projection image by applying, to an output signal from the detector, logarithm conversion processing on a function deviating from an ideal logarithm function. The ideal logarithm function is a logarithm function defined by a mathematical formula of $y=K \cdot \log[b, x]$ (wherein a variable x is an input, a variable y is an output, and a reference K shows a scaling constant). The function deviating from the ideal logarithm function has an input/output characteristic deviating from that of the ideal logarithm function. Such deviating function is for example a linear function and applied to a conversion of only low-count data into its projection data to suppress low-count artifacts on reconstructed CT images.

19 Claims, 6 Drawing Sheets

X-RAY CT SCANNER CAPABLE OF PERFORMING IMPROVED LOG CONVERSION

BACKGROUND OF THE INVENTION

1. Technical Field of the Invention

The present invention relates to an X-ray computed tomography scanner in which low-count data, which is acquired when an X-ray passes through object's regions whose X-ray absorption coefficients are relatively higher, is effectively used for CT image reconstruction.

2. Description of Related Art

As is well known, X-ray computed tomography (CT) is an imaging technique of producing density images based on X-ray absorption coefficients. An X-ray is radiated toward an object along various radiation angles to scan a section of the object so that resultant X-ray transmission amounts are measured, and X-ray absorption coefficients at each position in the object's section are computed. Using the coefficients, density images are produced. From a different viewpoint, it can be said that the X-ray CT makes use of the fact that the living body is composed of various tissues different in their X-ray absorption coefficients.

In performing the X-ray CT imaging, some regions in a scanned object's section, such as bones, provide higher X-ray absorption coefficients. Such regions are also subjected to X-ray measurement, but amounts of X-ray from the regions, which are detected by an X-ray detector, are extremely low, thereby frequently causing a considerable amount of reduction in the SNR.

An X-ray decays in strength exponentially while traveling through an object. An X-ray detector detects incoming X-rays and outputs signals in proportion to their transmission amounts. The output signals from the detector enter a data acquisition system (DAS), wherein the signal is amplified by amplifiers concurrently with being converted to digital signals by A/D converters.

To obtain projection data composed of a total sum of X-ray absorption coefficients computed along each X-ray path, it is required that the digitized output signals undergo processing called "log conversion" carried as part of the pre-processing for the output signal.

However, the output signals have already contained noise components at the stage of the log conversion. Such noise components include random noise attributable to the detector and DAS.

The random noise is normally negligible, differently from photon noise (serious noise caused by fluctuations in the number of incoming X-ray quantum particles). However, it is not always light to neglect the random noise. Particularly, in cases where, under particular conditions, such as scanning of thinner slices or scanning under lower X-ray amounts, X-rays that have been transmitted through paths of which X-ray absorption is large are detected by a detector, the random noise at the detector is often larger in strength than the photon noise. In such a case, the random noise becomes a dominant in the noise of the output from the detector. Even when no random noise is originated from the detector and DAS, if an amount of incoming X-rays is remarkably low, the amplitude of noise included in the output signal from the detector reaches an unnegligible level, compared to an average level of the output signal.

In the present application, regardless of whether the primary cause is photon noise or noise from the detector and DAS, the signal that contains noise of an unnegligible level compared to an average level of the signal is called "low-count data."

When reconstructing images with the use of acquired data that contains such low-count data in the conventional manner, many streak artifacts (hereafter referred to as "low-count artifacts") appear along path directions passing a region where X-ray absorption is larger. The low-count artifacts make it difficult to use such images for diagnosis.

The study about the low-count artifacts, which was conducted by the present inventors, showed that the foregoing log conversion has the nature of amplifying the noise contained in the low-count data. In other words, the conventional log conversion will deteriorate the originally-lower S/N of the low-count data, thereby accelerating the appearance of the local-count artifacts on images.

SUMMARY OF THE INVENTION

The present invention has been made in consideration of the foregoing conventional problems, and an object of the present invention is to eliminates or suppress the low-count artifacts.

In order to realize the foregoing object, as one aspect of the present invention, there is provided an X-ray CT scanner comprising: an X-ray source generating an X-ray; a detector detecting the X-ray generated by the X-ray source and transmitted through an object; a processor producing projection data by applying to an output signal from the detector logarithm conversion processing on a function deviating from an ideal logarithm function; and a reconstruction unit configured to reconstruct an image using the projection data produced by the processor.

An X-ray CT scanner according to the present invention will not stick to the conventional log conversion in producing projection data. The inventors' study into the log conversion revealed that an improved log conversion with the use of a function made to deviate positively in a certain manner from the ideal logarithm function is highly effective for "low-count data" acquired by the detector. It is therefore to eliminate or suppress low-count artifacts from or on reconstructed CT images.

Preferably, the ideal logarithm function is a logarithm function defined by a mathematical formula of $y = K \cdot \log[b, x]$ (wherein a variable x is an input, a variable y is an output, and a reference K shows a scaling constant), wherein the function deviating from the ideal logarithm function is configured to have an input/output characteristic deviating from an input/output characteristic defined by the ideal logarithm function.

Still preferably, the function deviating from the ideal logarithm function consists of a function range assigned to the inputs equal to or larger than a specified value and defined by the ideal logarithm function, and a further function range assigned to the inputs less than the specified value and formed to have the deviating input/output characteristic. By way of example, the function range and the further function range are defined individually and separated at a threshold given to the inputs.

It is also preferred that the function deviating from the ideal logarithm function is defined as a function providing one curve consisting of both of the function range and the further function range. For example, the processor includes a table where input/output data of the one curve are stored and reference means configured to perform the logarithm conversion processing with reference to the input/output data stored in the table.

It is also preferred that the processor has weighting means configured to perform the logarithm conversion processing by performing weighted summation of plural log conversion results.

Still it is preferred that the further function range is smaller in an angle of the input/output characteristic than the function range.

DETAILED DESCRIPTION OF PREFERRED EMBODIMENTS

Referring to the accompanying drawings, preferred embodiments of an X-ray CT (computed tomography) scanner according to the present invention will now be described.

There are a variety of types of X-ray CT scanners, which includes a "rotate/rotate" type in which both of an X-ray tube and an X-ray detector rotate around an object as one unified member and a "stationary/rotate" type in which a multitude of detection elements arrayed on a ring are fixed but only an X-ray tube rotates around an object. The present invention can be applied to any type of X-ray CT scanner. The present embodiment will now be described about the rotate/rotate type of X-ray CT scanner, which is the current mainstream.

Figure 1:
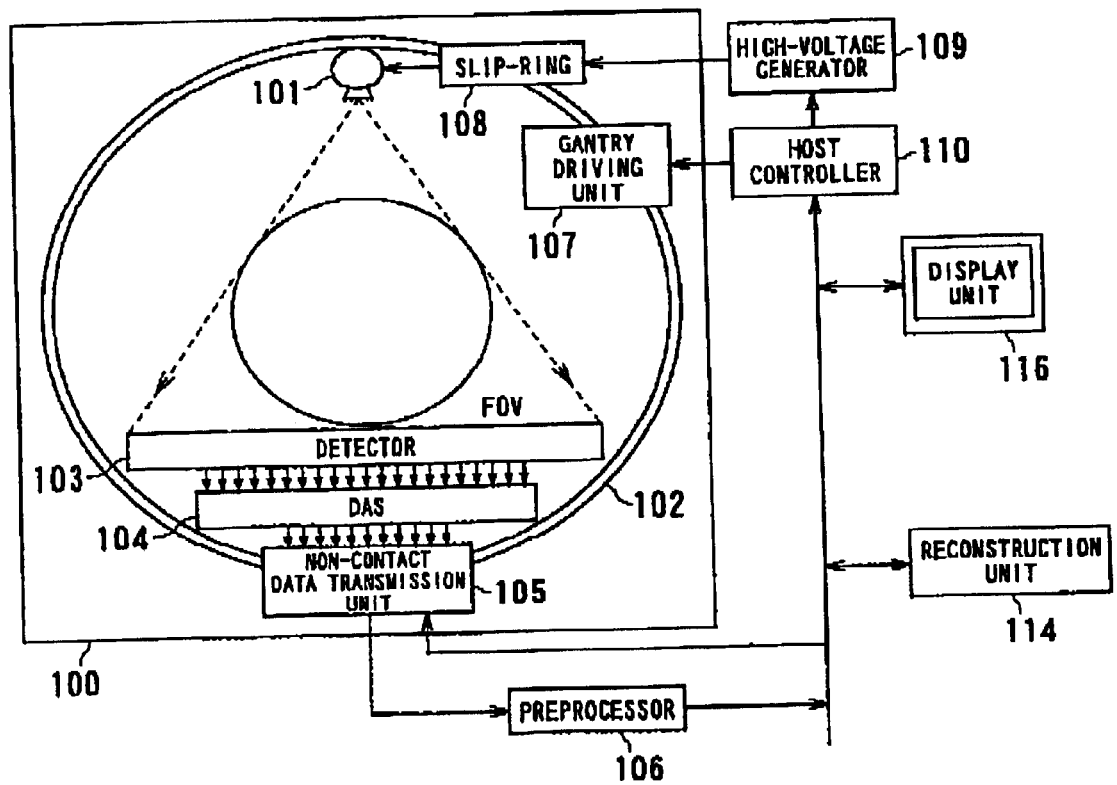
FIG. 1 is a schematic diagram showing an X-ray CT (computed tomography) scanner according to an embodiment of the present invention.

As shown in FIG. 1, an X-ray CT scanner according to a first embodiment has a gantry 100 including therein an X-ray tube 102, X-ray detector 103, and ling-like rotation member 102. The rotation member 102 is driven by a gantry driving unit 107 to rotate in a predetermined direction. On the rotation member 102 are provided the X-ray tube 102 and the X-ray detector 103 so that they are mutually faced.

The X-ray tube 101 receives high-voltage pulses from a high-voltage generator 109 via a slip-ring 108, thereby generating X-rays a fan-beam or cone-beam form. The radiated X-rays are transmitted to pass through a field of view (FOV) of an object placed at an imaging region, and are received by the X-ray detector 103. As is known, while traveling within the object, the X-rays decay exponentially correspondingly to X-ray absorption coefficients specific to bones, soft tissues, and/or others existing along their paths. The decayed X-rays then enter the X-ray detector 103.

The X-ray detector 103, which is formed into a multiple channel type, is equipped with a plurality of detecting elements arrayed in an arc form centered at the focus of the X-ray tube 101. The detector 103 detects the incoming X-rays at a constant particular sampling frequency, thus allowing the incoming X-rays to be converted electrical signals (i.e., electrical current) in proportion to their amounts at every view angle. The direction along which the X-ray detecting elements are arrayed is called a channel direction, the angular position of the X-ray tube 101 at each time of sampling is called a view angle, and the direction along which the view angle changes is called a view direction.

The X-ray detector 103 can be formed into either a single type of detector or a multiple type of detector. The former is configured by arranging one line of plural detecting elements arrayed in the channel direction in a body-axis direction perpendicular to the channel direction. The latter is configured by arranging a plurality of such element lines in the body-axis direction.

The electrical signals outputted from the X-ray detector 103 are sent to a data acquisition system (DAS), whereby the signals are converted into voltage signals, amplified, and converted to digital signals, before being sent a pre-processor 106 through an optical or magnetic non-contact data transmission unit 105. A contact type of transmission unit may be used in place of the non-contact data transmission unit 105. To raise the rate of transmitting data, the data is normally compressed down to a lower number of bits (for example, 16 bits) or to a lower number of channels before sending it. After sent to the preprocessor 106, the data is uncompressed up to its original number of bits or its original number of numbers.

As described, the acquired data should be subjected to a "log conversion" to obtain a total sum of X-ray absorption coefficients along each X-ray path, that is, X-ray projected information, because the X-rays have experienced exponential decays within an object during their travels. Though this log conversion is required by any type of X-ray CT scanner, the X-ray CT scanner of the present embodiment, to which the present invention is applied, adopts a log conversion of a different kind from the existing log conversion.

The preprocessor 106 is in charge of decoding data or expanding data if the compression is made before sending the data to the preprocessor 106. In addition, the preprocessor 106 is configured to perform various kinds of correction. Preferably, the correction includes offset correction, reference correction, and water correction. The offset correction is done to remove DC noise due to the DAS 104 (for instance, an input less than 1 is rounded up to 1). The reference correction is directed to eliminating fluctuations of the detected signals depending on changes in the view angle that is attributable for temporal changes in the X-ray output. This reference correction corrects acquired data on the basis of reference data detected with the aid of a reference detecting element. The water correction is subtraction of previously acquired water phantom data from the acquired data, resulting in that differences in sensitivity between channels of the X-ray detector 103 are suppressed so that the CT value of water becomes a reference value of zero.

In the present embodiment, the data inputted to the preprocessor 106 (that is, the data just before being subjected to the log conversion and the various kinds of correction) is called "pure-raw data," while the data outputted from the preprocessor 106 (that is, the data just after having experienced the log conversion and such kinds of correction and just being ready for reconstruction processing) is called "raw data." Both the terms "pure-raw data" and "raw data" should be differentiated distinctively.

The raw data from the preprocessor 106 is sent to a reconstruction unit 114, where the pre-processed raw data is used for reconstruction of CT images, such as tomographic images, three-dimensional surface images, and/or MPR (multi-planar reconstruction) images. Image data is then delivered to a display unit 116 to display images. The display unit 116 is accompanied by an input device (not shown) whereby a user is able to provide the scanner with necessary information such as various imaging conditions.

A host controller 110 is responsible for control of the entire operations of the scanner, including scanning, relaying data, and processing of data.

The preprocessor 106 will now be detailed, which is the most characteristic component in the scanner because the present invention is practiced into the preprocessor 106.

The present invention, which is applied to the X-ray CT scanner of this embodiment, is based on a concept that a logarithm function for conversion different from the conventional one is used. Considering this fact, why the conventional logarithm function is inconvenient will first be described, together with how the conversion using such logarithm function is made.

As described before, the "low-count data" is data showing as larger fluctuations due to noise as unnegligible compared to an average signal level. When the log conversion, which is non-linear processing, is applied to the low-count data, a conversion characteristic that has been expected is no longer obtained because of the noise. This problem derives from the fact the log conversion is depicted into a curve having a remarkable upward rise when drawn on input values (along the lateral axis) v.s. output values (along the vertical axis).

The general log conversion processing is based on the following the formula (1).

$$y = K \log[b, x] \quad (1),$$

wherein a variable "x" is an input that corresponds to pure-raw data, and a variable y is an output that corresponds to pure data. A symbol "b" is the base of a logarithm, such as "e", "10" or others. Preferably, in the computer's computation, the bottom is usually "2." A symbol "K" is a scaling factor used to define a range of the output values "y" in a desired manner for data processing, according to the base to be used or a range of the input values "x."

In the present invention, the logarithm function on the formula (1) is referred to as an "ideal logarithm function," while a log conversion based on the "ideal logarithm function" is referred to as an "ideal log conversion" or "normal log conversion." Also the present invention uses a function including a function region deviating from the ideal log function. For the reason that the remaining function range is, however, in accordance with the "ideal log conversion," the conversion processing with the aid of such function including a deviating function range is also called "log conversion," like the case of the ideal log function.

In the formula (1), an input "x" is an average <x>, where the symbol "< >" expresses an average. When it is assumed that noise fluctuations are not so smaller than an average <x> and the input "x" is x1=<x>+α due to noise, wherein "α" is a positive value, a log conversion on the formula (1) gives an output y1=log(<x>)+β. In the case that the input "x" is x2=<x>−α, the log conversion gives an output y2=log(<x>)−γ. The gradient of the log conversion curve is more moderate for inputs equal to or larger than a value of <x>, while it is steeper for inputs less than the value of <x>, with the result that "γ" is always greater than "β." In cases where the low-count data of which value of <x> is not sufficiently large compared to "α," "γ" is extremely different in value from "β." Thus, when there is noise where the input "x" is less than <x>, the output "y" becomes a value of which noise component is more enhanced through the log conversion. This will bring about more enhanced low-count artifacts.

In order to prevent such an undesired situation, in the present invention, the pure data that have been digitized and amplified by the data acquisition system 104 (and received the non-contact data transmission unit 105) are subject to the conversion processing on a function deviating from the normal logarithm function. Precisely, such conversion function of which range directed to the low-count data deviates from the ideal logarithm function.

Incidentally, it has been normally considered that a change in the logarithm function will lead to a problem of deteriorating the CT values. But this problem is not always true of the low-count data. As to the low-count data, a change in the logarithm curve will not necessarily worsen the CT values. When the low-count data that contains noise components is subjected to the log conversion based on the formula (1), its average <y> of the log-converted outputs always differs from "K log [b, <x>]," which is resulted from the log conversion of an input average <x>, owing to an asymmetric response to noise. This difference is clear from the fact that the log conversion is nonlinear processing. Accordingly, it can be understood that, as to the low-count data, the log conversion on the foregoing formula (1) has caused the CT value problem practically, but low-count artifacts have simply hidden the CT value problem. Carrying out a conversion that enables the computation of a value almost equal to "K log [b, <x>]" statistically will suppress the CT value problem, rather than a simple computation based on the formula (1). Even from this point of view, it is preferred to have the log conversion shifted from the formula (1).

If the deviation is made in a poor manner or there occurs abnormal situations where an average <x> of the input signal "x" is almost zero, there is a possibility that the CT value problem will become worsened more seriously, even beyond a tolerance level. However, the experiment conducted by the present inventors showed that there could be obtained a function for a log conversion that is capable of normally suppressing low-count artifacts, with the CT value problem surely limited within a tolerance level.

Figure 2:
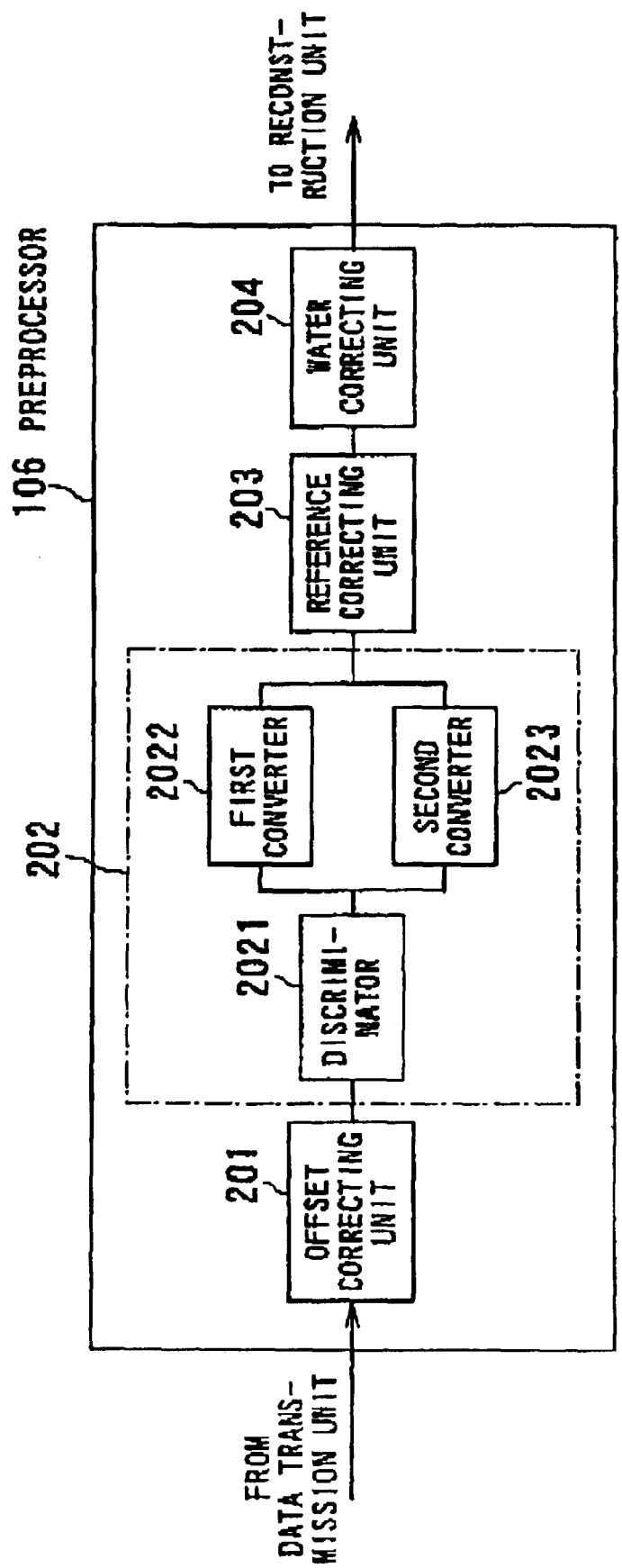
FIG. 2 shows the block diagram of a pre-processor employed in the embodiment.

FIG. 2 details the preprocessor 106 in charge of performing the above log conversion according to the present invention. In the preprocessor 106, other than the log conversion, it is preferred that an offset correction, reference correction, and water correction are performed, but those corrections are omitted from being detailed.

As shown in FIG. 2, the preprocessor 106 is equipped with an offset correcting unit 201, signal converter 202, reference correcting unit 203, and water correcting unit 204. The offset correcting unit 201 is used to remove DC noise generated and mixed at the DAS 104. The signal converter 202, which is an essential part for realizing the present invention, is in charge of conversion of low-count data based on a function deviating from the curve written by the ideal logarithm function. The reference correcting unit 203 is directed to a reference correction of a signal converted at the signal converter 202. The water correcting unit 204 is placed for a water correction of a signal coming from the reference correction unit 203.

The signal converter 202 is provided with, as shown in FIG. 2, a discriminator 2021 for determining data using a threshold and a first and second converters 2022 and 2023 which are in charge of a log conversion respectively depending on the discriminated results at the discriminator 2021.

Specifically, the discriminator 2021 is configured to determine if data (i.e., pure-raw data) from the offset correcting unit 201 is low-count data or not with reference to a threshold, then supplies the pure-raw data to either the first or second converter 2022 or 2023 in compliance with the determined results.

In cases where the discriminator 2021 determines that the received pure-raw data is not low-count data, that is, it is non-low-count data, such data is sent to the first converter 2022, where the pure-raw data is subjected to log conversion based on the ideal logarithm function. By contrast, when the discriminator 2021 determines that the received pure-raw data belongs to low-count data, such data is sent to the second converter 2023. At the converter 2023, the pure-raw data is subjected to data conversion based on a function of which conversion values to the low-count data is different from the ideal logarithm function.

The discriminator 2021 has a threshold to estimate whether pure-raw data is low-count data or not. Preferably, the threshold is set in consideration of random noise from the detecting components such as photodiodes and DAS components such as DAS 104. By way of example, the threshold is pre-set as a fixed value or specified as variable values. Further, a preferred example is that the threshold is specified in association with a variety of types of imaging conditions, such as a gain at the DAS 104 and/or the width of slices to be imaged. And it is particularly preferred that the threshold is changed in association with operative conditions of the DAS 104. In the example of FIG. 2, the threshold for switching over the input to either the first or second converter 2022 or 2023 is changed in accord with imaging conditions. This makes it possible to steadily realize conversion processing in accord with imaging conditions including gains assigned to the DAS 104, whereby more deeply suppressing low-count artifacts.

Further, in the case that the same gain is applied to all the channels of the DAS 104, the threshold can be decided according to the gain. However, when a different gain is applied to each channel, the threshold may be decided channel by channel.

Hence the discriminator 2021 is able to perform the determination on the threshold(s). That is, if the value of an input signal is equal to or greater than the threshold, the input is sent to the first converter 2022, while if the opposite case is realized, the input is sent to the second converter 2023.

The first converter 2022 is in charge of the log conversion on the ideal logarithm function. Namely, when the input signals whose amplitudes are greater than the threshold (that is, non-low-count data) come from the discriminator 2021, the first converter 2022 performs the log conversion based on the ideal logarithm function according to the formula (1), which has been used conventionally.

Meanwhile, when the second converter 2023 will receive from the discriminator 2021 the input signals whose amplitudes are lower than the threshold, which is low-count data. The second converter 2023 then performs the log conversion based on a function whose region applied to the low-count data is different from the ideal logarithm function used by the first converter 2022.

Such a function, which differs from the ideal logarithm function and is in charge of the low-count data, should be connected, at a point of the threshold in a step-less manner, to part of the ideal logarithm function in charge of the non-low-count data. In addition, such a function deviating from the ideal logarithm function should be lower in its curve gradient for most low-count data, in comparison with that of the ideal logarithm function. There are various such functions, which include n-th degree polynomials, for example. The simplest form of such polynomials is a linear function of y=ax+b.

Figure 3:
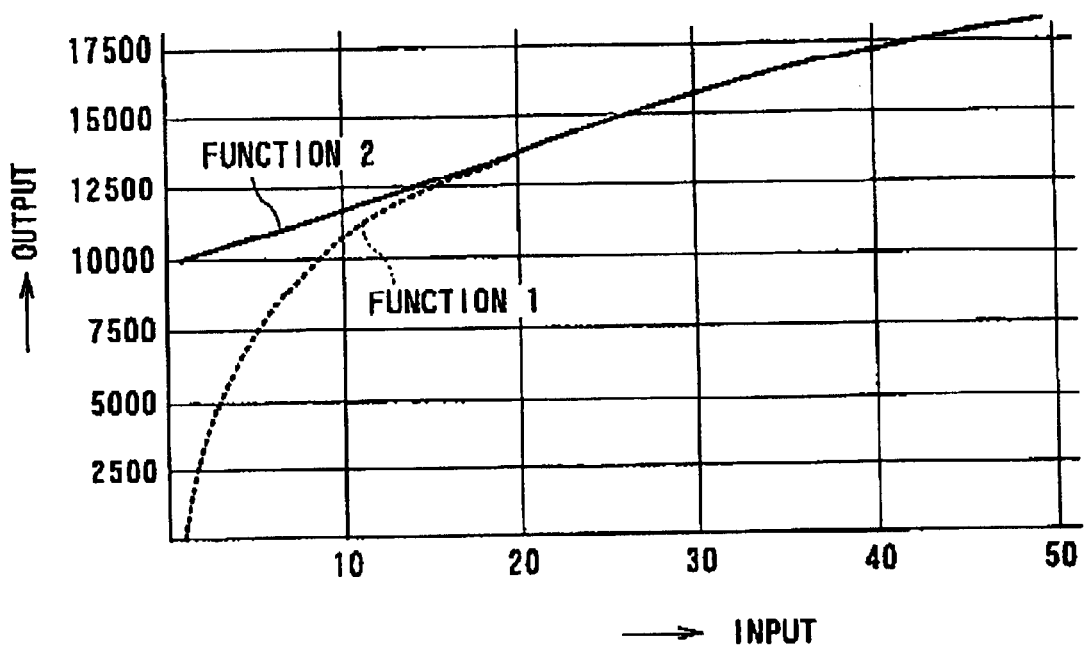
FIG. 3 explains a conversion function consisting of two functions, which is used in the embodiment.

FIG. 3 exemplifies, on condition that a threshold of "20" for the inputs is given at the discriminator 2021, an ideal logarithm function "1" employed by the first converter 1022 and the linear function "2" employed as a converting function by the second converter 2023. The linear function "2" uses, as its gradient "a," a gradient (differential coefficient) of the function "1" obtained at the point of the threshold. The intercept "b" of the function "1" is decided so as to accomplish no separation between the two functions "1" and "2" at the point of the threshold.

Figure 4:
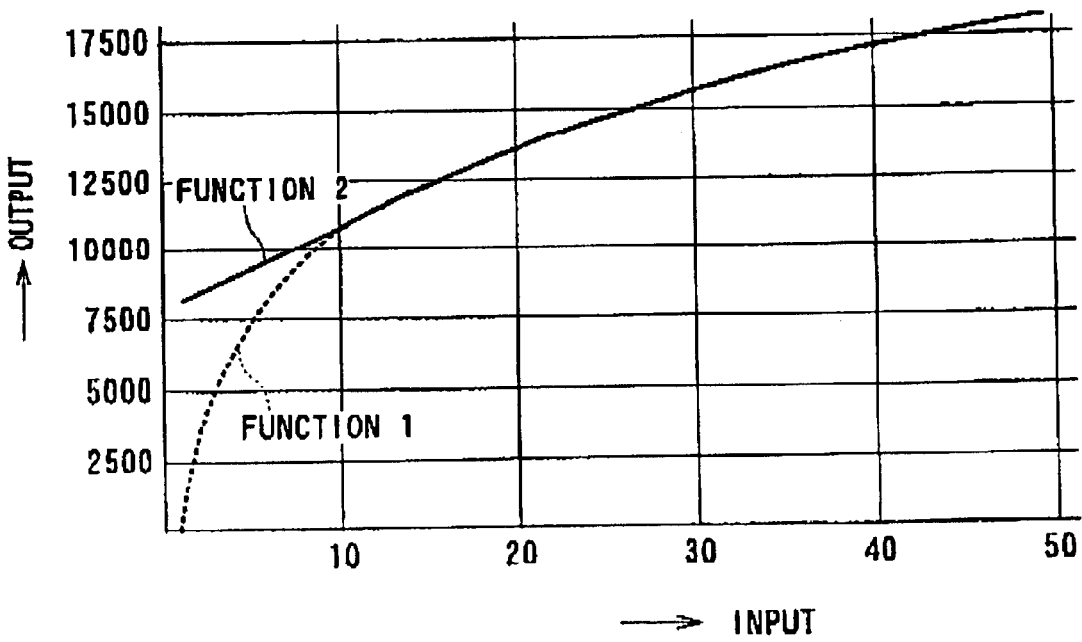
FIG. 4 explains a further conversion function consisting of two functions, which is used in the embodiment.

The threshold can be selected to some extent in a free manner. Further, the gradient "a" is not always limited to the differential coefficient of the function "1" at the point of the threshold. FIG. 4 shows another example of such functions "1" and "2", in which one function "1" is the ideal logarithm function and the other function "2" is realized by a linear function, on condition that the threshold is placed at a point "10" in the inputs. In this case, the function "1" is set to have a gradient "a" smaller than the differential coefficient of the function "1" at the threshold.

Conventionally, the ideal logarithm function "1" shown in FIGS. 3 and 4 has been used alone to perform the log conversion of the pure-raw data, which has further deteriorated the low-count data. In contrast, in the present embodiment, only when the values of input signals (i.e., pure-raw data; more precisely, non-low-count data) are equal to or higher than a predetermined threshold, the ideal logarithm function "1" is used for the log function. However, when the values of input signals are lower than the threshold (i.e., low-count data), the function "2" deviating from the ideal logarithm function "1" is assigned to the log conversion of pure-raw data.

The pure-raw data that has been log-converted are subjected to the remaining pro-processing (such as the reference correction and water correction), before being sent to the reconstruction unit 114 where the data is reconstructed into images.

As described above, the present embodiment is characterized in that a function deviating from the ideal logarithm function is applied to only the low-count data (pure-raw data) from the detector. To attain this selective conversion, the discriminator 2021 is used to determine whether the pure-raw data is low-count data or not. If the low-count data is provided, the log conversion is carried out based on the second logarithm function (i.e., the linear function in the above embodiment). Meanwhile, when the non-low-count data is given, the log conversion is carried out on the first logarithm function (i.e., the ideal logarithm function), which differs from the second one.

The low-count data is usually obtained when X-rays pass object's regions of which X-ray absorption coefficients are relatively higher, such as shoulders, back bones, or lumbar. Even when such low-count data undergoes the image reconstruction processing, low-count artifacts can steadily be eliminated or suppressed from or in the reconstructed images.

Moreover, in cases where the threshold is changed depending on imaging conditions, such as gains at the DAS 104, a field of view (FOV), and/or slice thicknesses (that is, pieces of information in which noise levels of the data acquisition components are reflected), the low-count artifacts in images can be reduced more steadily.

If the threshold is changed as described above, it is preferred that the function "2" is changed as well. For example, when the function "2" is set to a linear function, at least one of its gradient and its intercept is changed responsively to changes in the value of the threshold.

(Other Embodiments)

The present embodiment will not be limited to the above embodiment and may be modified in further modes within the scope of claims of the present invention.

By way of example, the two type of functions, which are the first function used by the first converter 2022 and the second function used by the second converter 2023, can be replaced by only one type of function having the same effect as that described above. If such a configuration is adopted, the discriminator 2021 becomes unnecessary, while the first and second converters can be unified into one unit. The unified one conversion unit may be configured to have a single log conversion characteristic (i.e., a signal function) approximating to the entire solid-line curve shown in FIG. 3 or 4. Such a single function can be realized by a single n-th degree polynomial having a greater degree "n."

Other examples of such a single function for log conversion can be accomplished by a conversion on filtering and a conversion on a memory table.

Figure 5:
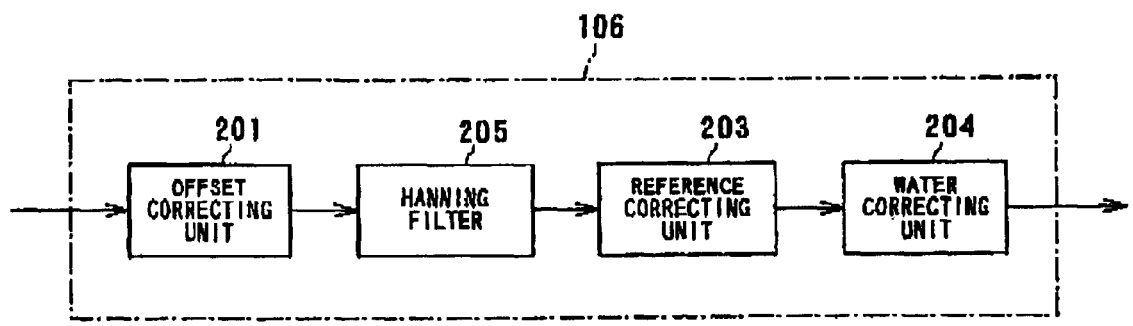
FIG. 5 is the block diagram of a preprocessor according to a modification of the present embodiment.

In the former, as shown in FIG. 5, the preprocessor 106 is provided with the offset correcting unit 201, a hanning filter 205, the reference correcting unit 203, and the water correcting unit 204 in this order. The units other than the hanning filter 205 are the same in the configurations as those shown before.

The banning filter 205 will now be explained. The hanning filter 205 is responsible for a conversion (i.e., log conversion) based on a single-function input/output characteristic indicated as shown in FIG. 6 by a single curve smoothly connecting a function range tracing the ideal logarithm function "1" and a function range tracing the function "2" deviating from the ideal logarithm function "1."

Figure 6:
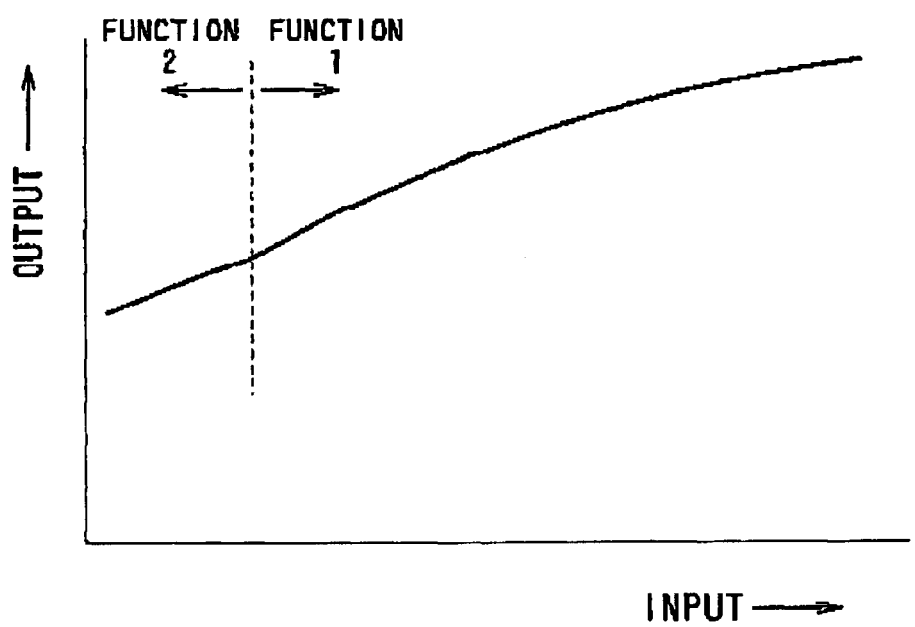
FIG. 6 pictorially shows a unified function of an ideal logarithm function and a function deviating from the ideal logarithm function, which explains another example of the conversion function.

In order to realize this function, the hanning filter 205 includes processing configurations for both the functions "1" and "2," although not shown in FIG. 6. The configurations allow each input "x" to be first subjected to processing on the function "1" (namely, an output "y1" is produced) and further processing on the function "2" (namely, a further output "y2" is produced), then allow the resultant outputs "y1" and "y2" to be subjected to a computation of an output y=(1−w)y1+w·y2, wherein "w" is a weighting factor. The weighting "w," which depends on the input "x," becomes "1" when the input "x" is small, while it becomes "0" when the input "x" is large.

One typical example of weighting functions that provide such a smooth transition of weighting is a hanning function, so that, in the present modification, the conversion unit 205 is representatively called a "hanning filter."

Accordingly, the "hanning filter 205" permits both the functions "1" and "2" to be designed freely and connected to each other smoothly. This eliminates the necessity of employing the processing based on the threshold, and makes it possible to handle in a practical way both the functions (1) and (2) as a single function.

Figure 7:
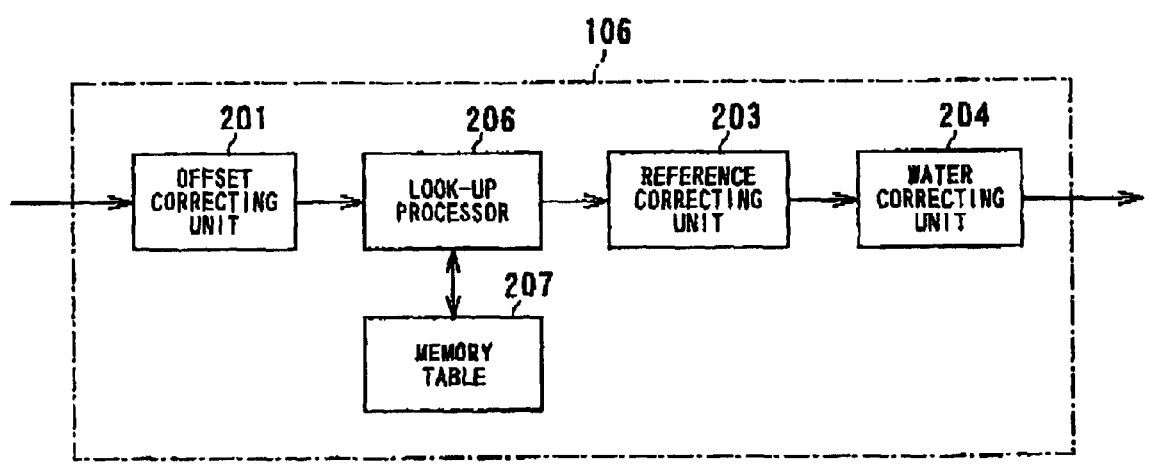
FIG. 7 shows the bloc diagram of a preprocessor according to another modification.

The latter modification is shown in FIG. 7, in which the preprocessor 106 has a look-up processor 206 and a memory table 207, both of which are placed between the offset correcting unit 201 and the reference correcting unit 203. In the memory table 207, values are memorized in a list form, which indicate the input/output characteristic of a single function formed by uniting the functions "1" and "2" shown in FIG. 6. The look-up processor 206 is configured to make reference to the input/output characteristic in the memory table 207, so that a log conversion of the signals from the offset correcting unit 201. The resultant log-converted data is then sent to the next reference correcting unit 203.

Another modification will now be explained with reference to FIGS. 8 and 9. The foregoing embodiment has been explained in the situation where only one threshold is used, but the log conversion according to the present invention can further be performed with a plurality of thresholds, which allows three or more functions to be switched over one from another.

Figure 8:
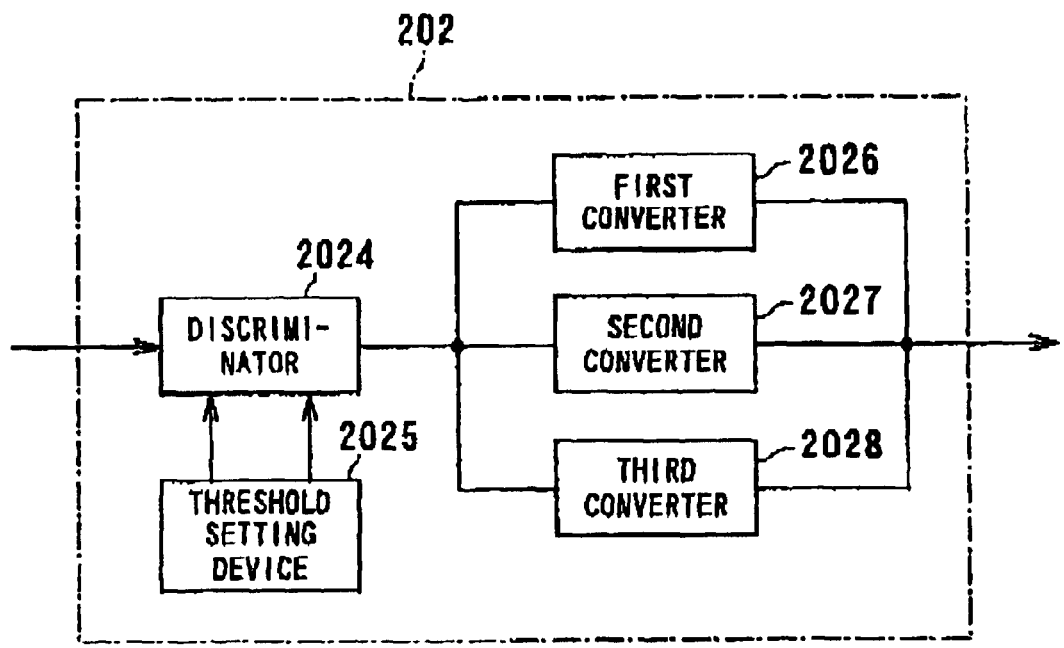
FIG. 8 shows the block diagram of a signal converter according to another modification.
Figure 9:
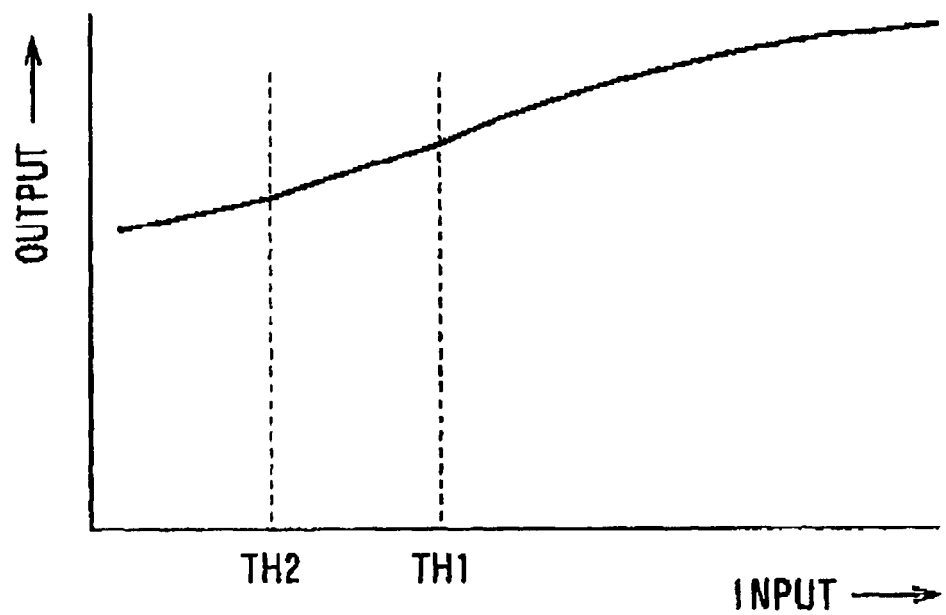
FIG. 9 pictorially exemplifies a unified conversion function consisting of three functions with two thresholds.

For instance, as shown in FIGS. 8 and 9, the signal converter 202 is equipped with a discriminator 2024, threshold setting device 2025, and first to third converters 2026 to 2028. As shown in FIG. 9, the threshold setting device 2025 is able to give, before the actual processing, the discriminator 2024 two thresholds TH1 and TH2 (<TH1) to discriminate the input signals. The one curve shown in FIG. 9, which are obtained by uniting three or more functions, has two ranges. One range shows a function of which inputs are equal to or more than one threshold TH1 and which is in accordance with the ideal logarithm function "1." The other range, which exists below the threshold TH1 for the inputs, complies with a function "2" deviating from the ideal logarithm function. The latter range according to the function "2" is further divided by the remaining threshold TH2. The region below the threshold TH2 is lower in the gradient than the range existing between the thresholds TH1 and TH2, thereby providing a gentler input/output characteristic. This modified configuration with a plurality of thresholds provides more desirable log conversion property for the low-count data.

Another modified configuration is also concerned with the signal converter 202 shown in FIG. 2. A plurality of types of converting functions, which are set to at least one of the first function used in the first converter 2022 and the second function used in the second converter 2023, can be stored in their inner memories correspondingly to imaging conditions such as gains in the DAS 104, FOVs, and/or slice widths. And if a certain imaging condition is selected, the functions used in the first and/or second converters 2022 and 2023 can be switched over in conformity with the selected imaging condition. Concurrently, the thresholds may be changed in the same manner as above.

Still another modification is provided as to locating the signal converter 202. In the foregoing embodiment, the signal converter 202 is located to perform the log conversion with the pure-raw data sent from the detector, the position of the signal converter 202 may be changed to other ones, as long as the foregoing log conversion is assured. One example is that the signal converter 202 is located immediately after the reference correcting unit 203.

Still, as for the procedures of data processing, there can be provided another modification. The foregoing embodiment has adopted the configuration in which the pure-raw data outputted from the DAS 105 through the non-contact data transmission unit 105 is sequentially sent to the preprocessor 106, thus the raw data being produced in sequence. Alternatively, in parallel to the preprocessor 106, a memory unit as well as a data reading/writing circuit may be provided, so that acquired pure-raw data is stored in the memory unit as it is, differently from the preprocessing. This makes it possible that, if necessary, the acquired pure-raw data is again read from the memory unit for preprocessing the newly read pure-raw data and then reconstructing images from the newly preprocessed data. Hence, when it is desired to scan again because of appearance of low-count artifacts on images under reconstruction, it is possible to immediately change the thresholds to be given the signal converter 202. Accordingly, this eliminates the necessity of repeating the scanning itself, whereby only the preprocessing is enough for a new observation of images.

The present invention may be embodied in other specific forms without departing from the spirit or essential characteristics thereof. The above embodiments and modifications are therefore to be considered in all respects as illustrative and not restrictive, the scope of the present invention being indicated by the appended claims rather than by the foregoing description and all changes which come within the meaning and range of equivalency of the claims are therefore intended to be embraced therein.

What is claimed is:

1. An X-ray CT scanner comprising:
   an X-ray source generating an X-ray;
   a detector detecting the X-ray generated by the X-ray source and transmitted through an object;
   a processor producing projection data by applying to an output signal from the detector logarithm conversion processing on a function deviating from an ideal logarithm function; and
   a reconstruction unit configured to reconstruct an image using the projection data produced by the processor.

2. The X-ray CT scanner of claim 1, wherein the ideal logarithm function is a logarithm function defined by a mathematical formula of y=K·log [b, x] (wherein a variable x is an input, a variable y is an output, and a reference K shows a scaling constant),
   wherein the function deviating from the ideal logarithm function is configured to have an input/output characteristic deviating from an input/output characteristic defined by the ideal logarithm function.

3. The X-ray CT scanner of claim 2, wherein the function deviating from the ideal logarithm function consists of a function range assigned to the inputs equal to or larger than a specified value and defined by the ideal logarithm function, and
   a further function range assigned to the inputs less than the specified value and formed to have the deviating input/output characteristic.

4. The X-ray CT scanner of claim 3, wherein the function range and the further function range are defined individually and separated at a threshold given to the inputs.

5. The X-ray CT scanner of claim 4, wherein the further function range consists of a plurality of further function ranges divided at further one or more thresholds given to the inputs.

6. The X-ray CT scanner of claim 3, wherein the function deviating from the ideal logarithm function is defined as a function providing one curve consisting of both of the function range and the further function range.

7. The X-ray CT scanner of claim 6, wherein the processor includes a table where input/output data of the one curve are stored and reference means configured to perform the logarithm conversion processing with reference to the input/output data stored in the table.

8. The X-ray CT scanner of claim 6, wherein the processor has weighing means configured to perform the logarithm conversion processing by performing weighted summation of plural log conversion results.

9. The X-ray CT scanner of claim 3, wherein the further function range has a less steep inclination in the input/output characteristic than the ideal logarithm function at the inputs less than the specified value.

10. An X-ray CT scanner comprising:
    an X-ray source generating an X-ray toward an object;
    a detector detecting the X-ray transmitted from the object;
    a processor applying logarithm conversion processing to an output signal from the detector to produce projection data, the logarithm conversion processing being based on an ideal logarithm function and a function different from the ideal logarithm function; and
    a reconstruction unit configured to reconstruct an image using the projection data produced by the processor,
    wherein the processor includes selection means configured to select either the ideal logarithm function or the function different from the ideal logarithm function, dependently on the output signal from the detector.

11. The X-ray CT scanner of claim 10, wherein the function different from the ideal logarithm function is expressed by an n-th degree polynomial.

12. An X-ray CT scanner comprising:
    an X-ray source generating an X-ray toward an object;
    a detector detecting the X-ray transmitted from the object;
    a determining unit configured to determine if or not an output signal from the detector is low-count data;
    a conversion processing unit configured to perform a conversion of the determined low-count data on a first conversion function to produce a conversion of projection data and to perform non-low-count data on a second conversion function different from the first conversion function to produce the projection data, the non-low-count-data being determined by the determining unit as data excluded from the low-count data, and
    a reconstruction unit configured to reconstruct an image using the projection data produced by the conversion processing unit.

13. The X-ray CT scanner of claim 12, wherein the first conversion function is expressed by an n-th degree polynomial and the second conversion function is a mathematical logarithm function.

14. An X-ray CT scanner comprising:
    an X-ray source generating an X-ray toward an object;
    a detector detecting the X-ray transmitted from the object;
    a classifying unit configured to use a threshold to classify whether an output signal from the detector is either low-count data or non-low-count data;
    a conversion processing unit configured to perform a conversion of the classified low-count data on a first conversion function to produce projection data and to perform a conversion of the classified non-low-count data on a second conversion function different from the first conversion function to produce the projection data; and
    a reconstruction unit configured to reconstruct an image using the projection data produced by the conversion processing unit.

15. The X-ray CT scanner of claim 14, wherein the threshold is variable.

16. The X-ray CT scanner of claim 15, wherein the threshold is determined depending on an imaging condition.

17. The X-ray CT scanner of claim 16, wherein the imaging condition is information about amplification of the output signal from detecting elements of the detector, the amplification being carried out at a data acquisition circuit, placed between the detector and the determining unit, for acquiring the signal.

18. An X-ray CT scanner comprising:

an X-ray source generating an X-ray toward an object;

a detector detecting the X-ray transmitted from the object;

a storing unit configured to store a plurality of types of conversion processing for converting the output signal from the detector on the functions;

a setting device configured to set an imaging condition;

a determining unit configured to determine a threshold for switching the plurality of types of conversion functions stored in the storing unit depending on the imaging condition;

a conversion processing unit configured to perform conversion processing with an output signal from the detector to produce projection data by using a conversion function switchably determined from the plurality of types of conversion functions by the determining unit; and a reconstruction unit configured to reconstruct an image using the projection data produced by the conversion processing unit.

19. The X-ray CT scanner of claim 18, wherein the threshold consists of a plurality of thresholds.

* * * * *